United States Patent
Günther et al.

[11] 4,219,651
[45] Aug. 26, 1980

[54] BENZIMIDAZO-[1,2a]-QUINOLINES

[75] Inventors: Dieter Günther, Kelkheim; Rüdiger Erckel, Hofheim am Taunus; Horst Frühbeis, Kelkheim, all of Fed. Rep. of Germany

[73] Assignee: Hoechst Aktiengesellschaft, Fed. Rep. of Germany

[21] Appl. No.: 830,175

[22] Filed: Sep. 2, 1977

[30] Foreign Application Priority Data

Sep. 10, 1976 [DE] Fed. Rep. of Germany ....... 2640760

[51] Int. Cl.² .................. C07D 471/22; C09B 57/00
[52] U.S. Cl. ........................... 546/70; 546/48; 546/52; 546/41; 252/301.21
[58] Field of Search ............. 260/288 CF, 287 CF, 260/283 G; 546/70

[56] References Cited

U.S. PATENT DOCUMENTS

| | | | |
|---|---|---|---|
| 3,920,662 | 11/1975 | Troster | 260/283 S |
| 4,003,898 | 1/1977 | Gomm | 260/288 CF X |
| 4,042,591 | 8/1977 | Kaul | 260/272 |
| 4,077,960 | 3/1978 | Shimada et al. | 260/281 NH |
| 4,124,589 | 11/1978 | Gunther | 546/70 |

FOREIGN PATENT DOCUMENTS 2510528  9/1976  Fed. Rep. of Germany ........... 260/287

OTHER PUBLICATIONS

Stensby, "Optical Brighteners", pp. 80, 85–88, Soap & Chemical Specialities, Jul. 1967.
Morgan et al., Chemical Abstracts, vol. 33, 594⁹–596⁹(1939).

*Primary Examiner*—Nicholas S. Rizzo
*Assistant Examiner*—Diana G. Rivers
*Attorney, Agent, or Firm*—Connolly and Hutz

[57] ABSTRACT

Benzimidazo-[1,2-a]-quinolines of the formula

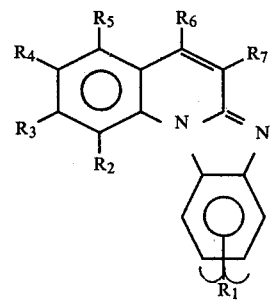

In the solid and dissolved state, the compounds of the invention are strongly fluorescing from reddish-blue to red, depending on the substitution. The compounds can be used as optical brighteners and as fluorescent dyestuffs. Furthermore they are valuable intermediates for the preparation of optical brighteners and fluorescing dyestuffs. They are distinguished by a very good fastness to light.

1 Claim, No Drawings

BENZIMIDAZO-[1,2-A]-QUINOLINES

The subject of the invention are benzimidazo-[1,2-a]-quinolines of the formula

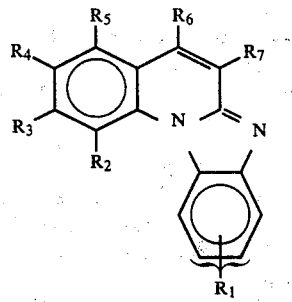

I in which $R_1$ is hydrogen, a lower alkyl or alkoxy radical, a halogen, nitro, amino, acylamino, lower mono- or dialkylamino-, lower trialkylammonium group or a carboxy or sulfo group optionally having modified functions, $R_2$ is hydrogen or a carboxyl group, optionally having modified functions, $R_3$ and $R_4$ each is hydrogen, lower alkyl or alkoxy, nitro, amino, acylamino or a carboxyl group optionally having modified functions, $R_5$ is hydrogen, a lower alkyl or carboxyl group optionally having modified functions, two adjacent radicals $R_2$, $R_3$, $R_4$, $R_5$ together may form the radical of a phenyl ring, $R_6$ is hydrogen, a lower alkyl or alkoxy group or a carboxyl group optionally having modified functions and $R_7$ represents the groups

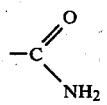

optionally substituted at N by lower alkyl groups or a phenyl group,

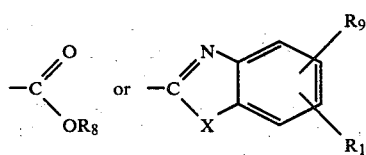

wherein X stands for O, S, NH or N—$R_{11}$ and $R_8$, $R_{11}$ each represent lower alkyl groups, preferably methyl and $R_9$ and $R_{10}$ each represent independent from one another hydrogen, lower alkyl or alkoxy, halogen, preferably chlorine or bromine, or a phenyl or naphthyl radical, $R_9$ and $R_{10}$, if in adjacent position, representing optionally a fused benzene ring together with the carbon atoms, to which they are bonded.

The subject of the present invention further is a process for the preparation of the compounds of the formula I, by condensing aldehydes of the formula

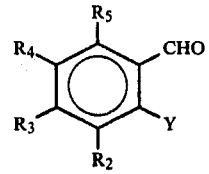

II wherein $R_2$ to $R_5$ are defined as above and Y represents a hydroxy, lower alkoxy, nitro or amino group or chlorine or bromine, with compounds of the formula

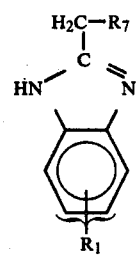

III in an inert solvent, at a temperature of from 80° to 200° C. and in the presence of from 0.1 to 5% by weight of a strong acid or an organic base, to obtain compounds of the formula IV

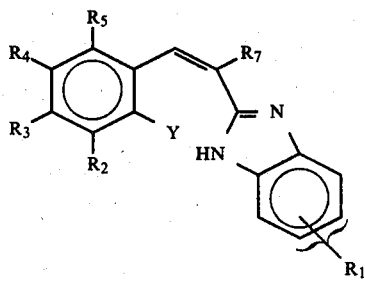

IV wherein $R_1$ to $R_7$ and Y are defined as above, and cyclizing the compounds obtained of the formula IV in an inert solvent at a temperature of from 110° to 300° C. to obtain compounds of the formula

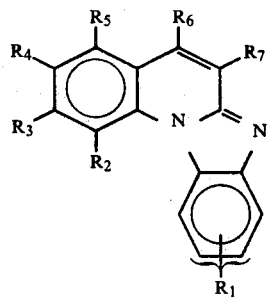

I

The term "lower" or "low molecular" in the above definitions with reference to aliphatic radicals is herein meant to be radcals having up to 6 carbon atoms, preferably up to 4, and especially up to 2 carbon atoms. Carboxyl groups having modified functions are the cyano group, the carboxylic acid ester group, especially phenyl ester and above all lower alkyl ester, in which case the lower alkyl esters may be substituted by hydroxy, lower alkoxy, lower dialkylamino or lower trialkylammonium groups; acid amides and acid hydrazides whose nitrogen atoms may be substituted by lower alkyl groups, two of those alkyl group being able to form together a saturated bivalent radical, preferably—together with the nitrogen atom which they are bound to—the pyrrolidine, piperidine, hexamethyleneimine, morpholine or piperazine radical.

Sulfo groups having modified functions are the sulfonic acid esters and the sulfonamides. Their definition is subject to the same conditions as mentioned for the carboxylic acid esters and the carbon amides cited above.

The condensation of the compounds II and III yielding the compounds IV is advantageously performed in a water-entraining solvent, preferably an aromatic hydrocarbon, especially benzene, toluene, xylene or in chloro- or dichlororbenzene, or in mixtures of these solvents, optionally with the addition of polar solvents, such as dimethylformamide or dimethylsulfoxide as solution promoters. The reactants are generally used in stoichiometric amounts, an excess of the aldehyde of the formula II may optionally be used. The reaction is generally performed at normal pressure at a temperature in the range of from 80° to 200° C., preferably of from 100° to 150° C., with addition of catalytical quantities of basic or acidic substances which are suitable for the Knoevenagel condensation, for example piperazine acetate, sulfuric acid, p-toluene-sulfonic acid or boric acid. The amounts used are generally in the range of from 0.1 to 5% by weight, preferably of from 0.5 to 2% by weight, calculated on the aldehyde of the formula II.

The compounds of the formula IV generally precipitate from the solvents used as crystals and can so be easily separated in pure form.

The starting compounds of the formula II are known in the literature. The compounds of the formula III are known from Chem. Rev. 74 (1974), 279 et seq.,French Pat. No. 1,580,823 and U.S. Pat. No. 3,105,837 or they may be prepared without difficulty in analogous manner to the processes disclosed in the above references.

The cyclization of the compounds IV yielding compounds of the formula I is generally performed at a temperature of from 110° to 300° C., preferably from 150° to 250° C., especially of from 180° to 220° C., in an inert solvent customary for use, for example chlorobenzene, o-dichlorobenzene, trichlorobenzene, toluene, xylene, tetralin, dekalin, methylnaphthalene, dimethylaniline, N-methylpyrrolidone, dimethyl sulfoxide, dimethylformamide, hexamethylphosphoric acid trisamide or mixtures of such solvents and optionally in the presence of basic catalysts. The basic catalysts which are preferably used are tertiary organic bases, for example piperidine, pyridine, N-dimethylaniline, triethylamine, piperidine acetate, piperazine, but mineral compounds, for example NaOH, KON, $Na_2CO_3$, $K_2CO_3$ may also be used, preferably in solvents miscible with water. These catalysts are generally used in an amount of from 0.1 to 5% by weight, preferably of from 0.5 to 2% by weight, calculated on the aldehyde of the formula II, higher amounts of catalysts being, however, possible. Those catalysts which have a boiling point in the range of the reaction temperature may also serve simultaneously as a solvent, for example dimethylaniline. Such a procedure is especially advantageous for starting compounds wherein Y represents an $NO_2$ group.

Reaction time depends on the chosen reaction temperature and on the nature of the substituents Y and $R_7$ and is generally in the range of from 15 minutes to 24 hours.

The condensation of the compounds II and III yielding compounds IV and the cyclization of the compounds IV yielding compounds I may be performed as described above in two steps, with isolation of the intermediary formed stage IV.

Especially at a temperature higher than 150° C., both reactions may take place in parallel manner, partially or completely, in one step. In this case, the final product may be obtained either directly by heating the starting compounds from 80° to 200° C. in an inert solvent and in the presence of from 0.1 to 5% by weight of a basic catalyst, as indicated above. This applies especially if Y in the starting compound II represents a hydroxy or alkoxy group or if $R_2$, $R_3$, $R_4$ or $R_5$ form together a fused benzene ring.

Stepwise operation is preferred, because of the purity of the products obtained. During the condensation YH or, if Y represents $NO_2$, nitrose-containing gases distill off.

In the benzimidazoles of the formula III the positions 5 and 6 are aquilvalent. The nitrogen atoms in the imidazole ring are also equivalent. So, in the condensation of II+III→IV→I isomer mixtures as well as homogeneous substances may be obtained. Since the position of $R_1$ in the molecule of the formulae IV or I cannot be predetermined and has not been known so far, the position of $R_1$ had been characterized as shown above.

The compounds of the formula I having one free amino group are prepared in known manner by starting either from the corresponding nitro compounds or from acetylamino compounds and reducing, preferably with iron in acid medium, or saponifying after condensation to obtain the desired compound of the formula I.

The compounds of the formula I obtained by condensing may be isolated in known manner, especially after cooling the reaction batch and complete crystallization, by suction-filtering and washing the filtered goods with a solvent of a lower boiling point, for example methanol or acetonitrile. For purification purposes, they may be recrystallized from one of the above solvents.

In the solid and dissolved state, the compounds of the invention are strongly fluorescent from reddish-blue to red, depending on the substitution. The compounds can be used as optical brighteners and as fluorescent dyestuffs. Furthermore they are valuable intermediates for the preparation of optical brighteners and fluorescing dyestuffs. They are distinguished by a very good fastness to light.

Substrates which are to be brightened or dyed are, for example, lacquers, natural and synthetic fibers, such as those made of natural or regenerated cellulose, acetylcellulose, natural or synthetic polyamides, such as wool, polyamide-6 and -6,6,polyesters, polyolefins, polyvinyl chloride, polystyrene or polyacrylonitrile, foils, sheets and films, bands or shaped articles made from such materials.

The compounds of the invention which are insoluble in water may be used as solutions in organic solvents or in aqueous dispersion, advantageously with the aid of the usual dispersing agents.

Depending on the application field and the desired effect, the amount of the compounds of the general formula I to be used, calculated on the material to be brightened or dyed, may vary within wide limits. It can easily be evaluated by tests and is generally within the range of about 0.01 to 2% by weight.

The compounds of the formula I which contain one or several nitro groups, are generally not fluorescing alone, but they can be converted by reduction, for example with iron, into the fluorescent amino compounds in a one step operation.

The following examples illustrate the invention:

EXAMPLE 1

248 g (1 mol) of di-benzimidazoly-2-methane and 136 g (1 mol) of 2-methoxybenzaldehyde are boiled in 1500 ml of toluene together with 5 g of piperidine acetate at the water separator, unitl 18 ml of water have been separated. The reaction product is suction-filtered in the cold state and washed with a small quantity of toluene. The residue is stirred with the addition of 2 of piperidine in 2500 ml of 1,2,4-trichlorobenzene for 5 hours at a temperature of from 205° to 210° C. and the evolved methanol is distilled off.

After suction-filtering at room temperature and washing with methanol there are obtained 284 g (85.5% of the theory) of a compound of the formula

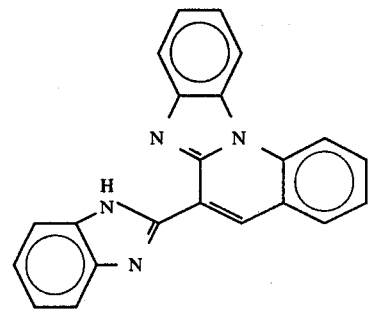

After recrystallization from dimethylformamide while clarifying with animal charcoal there are obtained light-yellow crystals having a melting point in the range of from 269° to 270° C.

$C_{22}H_{14}N_4$ molecular weight 334,4.

Mass spectrum M+/e: 334.

Absorption maximum (in DMF): 384 nm.

The compounds listed in the following table may be obtained by reaction in analogous manner to the above procedure:

TABLE

| Example | formula | Mp. (°C.) | absorption max. in DMF (nm) | yield (% of the theory) |
|---|---|---|---|---|
| 2 | | 280–281 | 393 | 85 |
| 3 | | 259–260 | 391 | 69 |
| 4 | | 142–143 | 370 | 56 |

TABLE-continued

| Example | formula | Mp. (°C.) | absorption max. in DMF (nm) | yield (% of the theory) |
|---|---|---|---|---|
| 5 | | > 300 | 399 | 86 |
| 6 | | > 300 | 403 | 84 |
| 7 | | 288–290 | 446 | 43 |
| 8 | | 289 | 403 | 84 |
| 9 | | 284–285 | | 76,8 |

TABLE-continued

| Example | formula | Mp. (°C.) | absorption max. in DMF (nm) | yield (% of the theory) |
|---|---|---|---|---|
| 10 | | 269–270 | | 55 |
| 11 | | 290–293 | 427 | 80 |
| 12 | | 290–291 | 420 | 85 |
| 13 | | 331–333 | 402 | 81 |
| 14 | | 285–287 | 384 | 74 |

| Example | formula | Mp. (°C.) | absorption max. in DMF (nm) | yield (% of the theory) |
|---|---|---|---|---|
| 15 | | 251–253 | | 80 |
| 16 | | > 335 | 394 | 65 |

EXAMPLE 18

10.8 (50 mmols) of 2-oxy-3-carboxy-naphthaldehyde-1 and 13.3 g (50 mmols) of benzimidazol-2-yl-benzthiazol-2-yl-methane are dissolved at elevated temperature in a mixture of 100 ml of xylene and 10 ml of dimethyl formamide and 0.5 g of piperidine acetate are added thereto. The reaction mixture is heated for 5 hours at boiling temperature at the water separator. After cooling, suction-filtering, washing with acetonitrile and drying, there are obtained 17.5 g (77% of the theory) of orange crystals of the formula

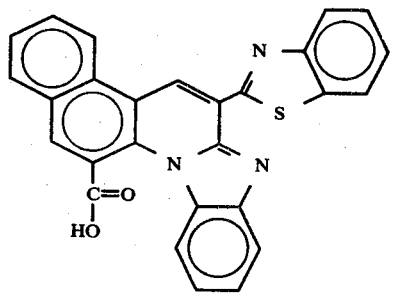

EXAMPLE 19

8 g (0.05 mol) of dibenzimidazolyl-(2)-methane and 10 g (0.05 mol) of 4-dimethylamino-2-nitrobenzaldehyde are boiled in 250 ml of toluene with 0.5 g of piperidine acetate at the water separator, until the $H_2$ evolution is terminated. The reaction product is suction-filtered in the cold state and washed with a small quantity of toluene. The residue is absorbed in 150 ml of dimethylaniline and stirred for 8 hours at reflux temperature, the cyclization being performed with splitting off of nitrosecontaining gases. After suction-filtering at room temperature and washing with methanol, there are obtained 9.3 g (65% of the theory) of the compound of the formula 7.

What is claimed is:

1. A compound of the formula

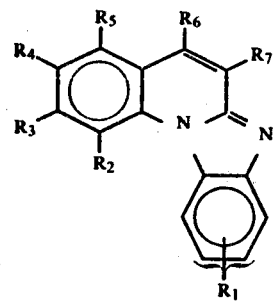

in which $R_1$ is hydrogen, $C_1$-$C_4$-alkyl, halogen, nitro, amino, $C_1$-$C_4$-alkanoylamino, mono- or di-$C_1$-$C_4$-alkylamino; $R_2$ is hydrogen, cyano, carboxy, carbo-$C_1$-$C_4$-alkoxy, carbonamido, mono- or di-$C_1$-$C_4$-alkylcarbonamido; $R_3$ and $R_4$ each is hydrogen, $C_1$-$C_4$-alkyl, $C_1$-$C_4$-alkoxy, nitro, amino, $C_1$-$C_4$-alkanoylamino, cyano, carboxy, carbo-$C_1$-$C_4$-alkoxy, carbonamido, mono- or di-$C_1$-$C_4$-alkylcarbonamido; $R_5$ is hydrogen; $R_6$ is hydrogen, cyano, carboxy, carbo-$C_1$-$C_4$-alkoxy, carbonamido, mono- or di-$C_1$-$C_4$-alkylcarbonamido and $R_7$ is the group

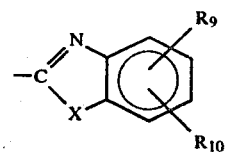

wherein X stands for O, S, NH or N—$R_{11}$ and $R_8$, $R_{11}$ are each $C_1$-$C_4$-alkyl, and $R_9$, $R_{10}$, each independent from one another, are hydrogen, $C_1$-$C_4$-alkyl, $C_1$-$C_4$-alkoxy, halogen, phenyl or naphthyl or $R_9$ and $R_{10}$ if in adjacent position, may form together a fused benzene ring.

* * * * *